United States Patent [19]

Forss et al.

[11] 4,277,626

[45] Jul. 7, 1981

[54] METHOD FOR THE ISOLATION OF VANILLIN FROM LIGNIN IN ALKALINE SOLUTIONS

[76] Inventors: Kaj G. Forss, Stahlbergintie 6 D, 00570 Helsinki 57; Esko T. Talka, Norotie 6 C, 01600 Vantaa 60; Kaj-Erik Fremer, Pajalahdentie 6 A, 00200 Helsinki 20, all of Finland

[21] Appl. No.: 115,048

[22] Filed: Jan. 24, 1980

[51] Int. Cl.³ .............................................. B01D 15/04
[52] U.S. Cl. .................................... 568/438; 210/672; 210/909
[58] Field of Search ................. 162/16; 210/24, 31 R, 210/31 C, 32, 38 R, 40, 656, 672, 909; 568/438

[56] References Cited

U.S. PATENT DOCUMENTS 3,197,359  7/1965  Logan ..................................... 162/16

*Primary Examiner*—Ivars C. Cintins
*Attorney, Agent, or Firm*—Andrus, Sceales, Starke & Sawall

[57] ABSTRACT

This invention relates to a method for the separation of low molecular-weight aromatic compounds, e.g. vanillin and dehydrodivanillin, from lignin, alkali, and from each other, in alkaline aqueous solutions. According to the method, the separation is effected by means of a cationic ion-exchange resin in its sodium salt form, e.g. of a strong sulphonic acid type or weak carbonic acid type, from which the substances adsorbed are removed by elution. The resin may be crosslinked to the extent of 2–16% divinylbenzene. The substances adsorbed onto the ion-exchange resin are appropriately eluted by either water alone, or by application of an aqueous sodium-salt solution (e.g. $Na_2CO_3$) followed by water.

6 Claims, 8 Drawing Figures

METHOD FOR THE ISOLATION OF VANILLIN FROM LIGNIN IN ALKALINE SOLUTIONS

This invention relates to a method for the separation of low molecular-weight aromatic compounds, e.g. vanillin and dehydrodivanillin, from lignin, alkali and from each other, in alkaline aqueous solutions by the aid of a cationic ion-exchange resin.

BACKGROUND OF THE INVENTION

It is known from prior art that vanillin can be manufactured from solutions with a content of lignosulphonic acids and their salts, for example from spent sulphite liquor, by air oxidation of the substrate mixed with either sodium hydroxide or calcium hydroxide plus sodium carbonate. After the oxidation, the vanillin thus formed from lignin is present in the alkaline solution as water-soluble sodium vanillate. The vanillin can be isolated from the oxidised solution by acidifying for example with carbon dioxide and sulphuric acid, separating the lignin precipitated, and extracting the vanillin by the aid of a suitable solvent, e.g. benzene or toluene, (Hibbert, H., Tomlinson, G., Jr., U.S. Pat. No. 2,069,185, Jan. 26, 1937.

Methods are also known, according to which the vanillin is extracted from the oxidised solution as its sodium salt by using a higher alcohol (e.g. n-butanol or isopropanol) (Sandborn, L. R., Salvesen, J. R., Howard, G. C., U.S. Pat. No. 2,057,117, Oct. 13, 1936; Bryan, C. C., Can. Pat. No. 528,837, Aug. 7, 1956).

It is also known that carbonyl compounds can be isolated by the aid of cation exchangers, on which the resin first is allowed to react with certain nitrogen-containing compounds, for example with hydroxylamine and hydrazine, which alter the chemical character of the resin in a way such that it is capable of reacting quantitatively with the carbonyl compounds (Töppel, O., U.S. Pat. No. 2,897,238, July 28, 1959).

A method of isolation is also known by which the sodium salt of vanillin is transformed into vanillin by the aid of weakly protonised cation exchange resins, which at the same time are transformed into their sodium salt modification.

The inherent disadvantage of the methods described above is the need of neutralisation in order to isolate the vanillin, with concurrent precipitation of the lignin, extraction of vanillin from large volumes of dilute vanillin solutions containing large amounts of precipitated lignin, chemical transformation of the ion exchange resin into a modification that makes it possible to effect adsorption, or regeneration of the ion-exchange resin into its original ionic modification after each batch.

SUMMARY OF THE INVENTION

In the present invention it has been noted that sodium vanillate can be adsorbed onto a cation exchanger in Na+-form direct from the oxidised alkaline solution.

The invention is characterised by the ion-exchange resin being in its same cation form all through the process, so that no separate regeneration step is required.

On the basis of the experiments made it has been established that large quantities of oxidised solution can be fed into the column whereby the lignosulphonates, sodium hydroxide and sodium carbonate are eluted before the sodium vanillate which is adsorbed onto the surface of the resin. The sodium vanillate adsorbed can later be eluted with either water or dilute alkali or alkali salt solution or by combination of these making it practicable to enrich the sodium vanillate for further treatment. Moreover, we have noted that by this procedure more than half of the alkali in the oxidised solution is recoverable along with the lignin. This liquor, freed from sodium vanillate, can be evaporated and the chemicals regenerated, whereby the alkali can be recycled to the sulphate pulp mill without raising the total sulphur content. We have also established that the amount of acid required for the neutralisation of the vanillate fraction has usually diminished by more than 60% from the original consumption, and that precipitation of lignin does not occur in connection with the neutralisation of the vanillate fraction. This is of considerable advantage, as in processes of vanillin manufacture according to current technology, the neutralisation and isolation of the vanillin from the lignin precipitated are considerable cost factors and present technical problems. If the substances adsorbed in the column are eluted with a sodium salt solution, the sodium vanillate can be separated also from other oxidation products.

DESCRIPTION OF THE PREFERRED EMBODIMENT

Figure 1:
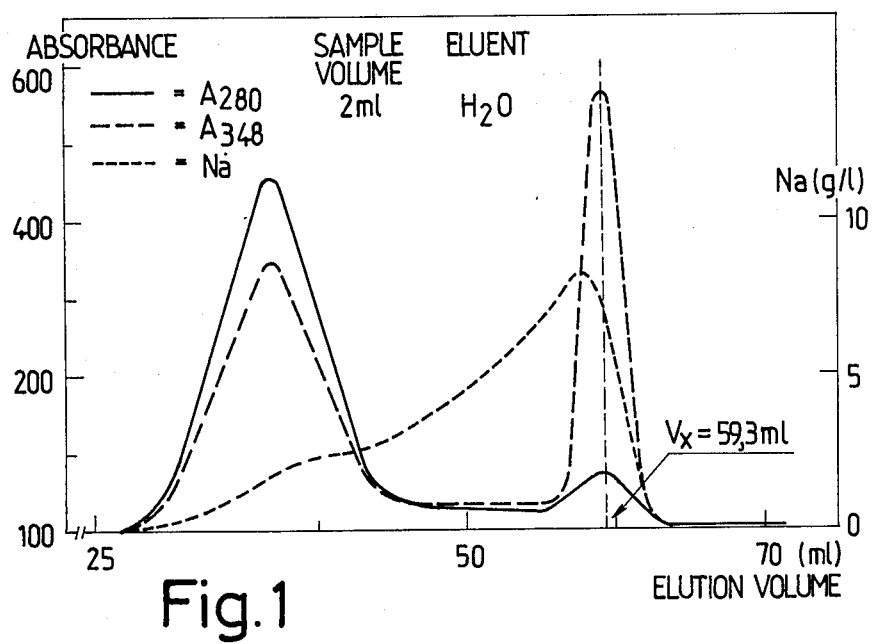
FIGS. 1–8 illustrate the elution of samples investigated through a column filled with a cation exchange resin in its Na+ modification.

The ion-exchange resins utilised in the experiments made have been either of the strong sulphonic acid type or cation-exchangers of weak carbonic acid type. Dowex-50W, X-8, has proved to be a particularly appropriate strong cation-exchanger owing to its low proportion of crosslinks, resulting in considerable contraction in NaOH-solution and swelling in aqueous solution. On the other hand, the adsorption of sodium vanillate onto the resin diminishes as the proportion of divinyl benzene crosslinks increases in the resin.

The invention is directable to any cation-exchange resin that can be transformed into Na+-modification and that unchanged withstands conditions under which the pH of the alkaline solution is higher than 10.

In the method covered by the present invention, the vanillin-containing lignin solution obtained in the oxidation-reactor is fed into a column filled with the cation-exchanger. The sodium vanillate and related substances become adsorbed onto the surface of the resin while sodium lignosulphonates, sodium hydroxide and sodium carbonate are eluted before the sodium vanillate. Solutions with a content of vanillin can be introduced into the column as long as adsorption takes place.

The oxidation products adsorbed onto the surface of the resin are eluted with water or with a suitable water solution that retains the resin in its Na+-form. Thus, no separate regeneration step is required. No precipitation occurs during the course of the adsorption and elution stages. Consequently, the oxidation products can be concentrated into a small quantity of eluant while, at the same time, the column is purified for the next adsorption stage.

The following examples are used in detailed description of the invention, but are not to be considered as limiting the scope of this invention to the amounts of substances, column measures, or running conditions cited in the examples.

EXAMPLE 1

A glass column, with a diameter of 2 cm and length of 40 cm, was mounted in an upright position so that a hose pump could be connected to the bottom of the column, making it possible to adjust the rate of flow of the solution. The column was filled with Dowex-50W, X-2 ion-exchange resin, 200–400 mesh, the height of the resin column being 25 cm. Prior to filling, the ion-exchange resin was transformed into its $Na^+$-form by treating it with sodium hydroxide solution (3 moles/liter).

2 ml of oxidised lignosulphonate solution, with a vanillin content amounting to 9,9 mg vanillin/ml, was fed into the column from the top at a rate of 21 ml/h (6,69 ml/h.cm$^2$). Since the absorptivity of vanillin in alkaline solution at 348 nm wavelength is 14,6 times higher than the absorptivity at 280 nm wavelength, the separation of sodium vanillate can be followed spectrophotometrically. The solution that had passed the column was collected as 4 ml fractions which were analysed for their content of sodium and for the separation of lignin from vanillate by measurement of the absorbances at 280 and 348 nm wavelengths, respectively.

When the 2 ml sample had flown into the column entirely, the run was continued by feeding distilled water into the column at the same rate. It was then noted that the lignin part moved in the column considerably faster than the vanillate part (FIG. 1). As the inner volume of the column was 26 ml, the main proportion of the lignin was collected within the elution volume range of 26–45 ml, while the sodium vanillate was collected within the elution volume range 55–65 ml. The sodium peak was located immediately before the sodium vanillate at 58 ml elution volume in a way such that 68% of the sodium contained in the sample had been eluted from the column prior to the vanillate fraction. The area of the vanillate region was determined by planimetry, and was 28 units.

The lignosulphonate fraction had been fully separated from the sodium vanillate and no precipitation was observed during the process.

EXAMPLE 2

Figure 2:
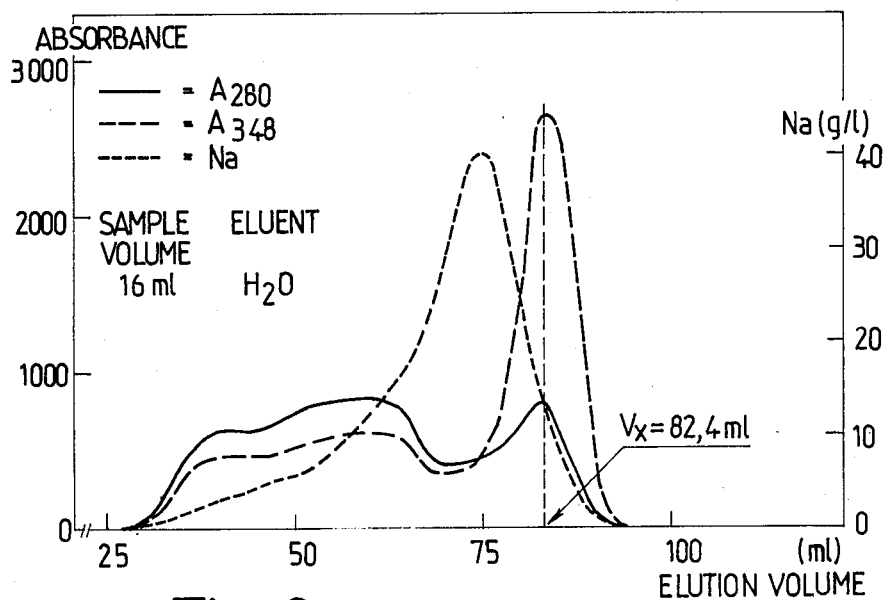

The procedure in Example 1 was followed, except that the volume of the sample was 16 ml. In this experiment, the lignosulphonate fraction broadened to extend over the elution volume range 26–75 ml. The vanillate fraction became eluted after this at the volume 75–90 ml (FIG. 2).

53,6% of the sodium was eluted before the vanillate region. The area of the vanillate region was 268 units. The vanillate fraction did not precipitate upon neutralisation with sulphuric acid.

EXAMPLE 3

Figure 3:
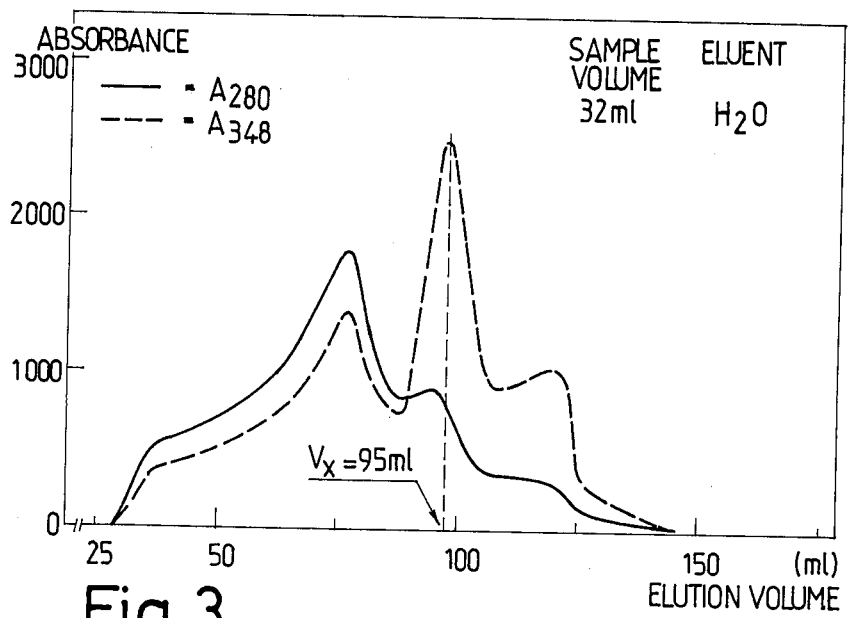

The procedure in Example 1 was followed, except that the volume of the sample was 32 ml. The lignin fraction broadened strongly to extend over the entire elution range. However, the main proportion of the lignin came out from the column prior to the sodium vanillate (FIG. 3). The lignin contained in the vanillate fraction did not precipitate upon neutralisation with sulphuric acid. The area of the vanillate region was planimetered to 528 units.

EXAMPLE 4

Figure 4:
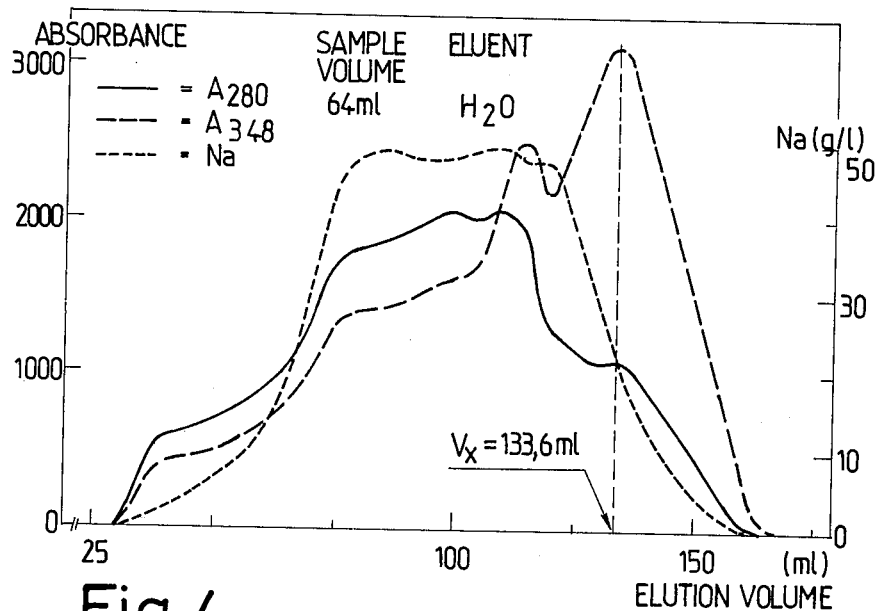

The procedure in Example 1 was followed, except that the volume of the oxidised lignosulphonate solution was 64 ml. Again, the lignin fraction broadened strongly; nevertheless, the vanillate fraction did not appear until after the lignin, at the elution volume 120–160 ml (FIG. 4). Since the column was incapable of adsorbing all of the sodium vanillate contained in the sample, two different peaks are observable in the vanillate region in FIG. 4, of which the larger peak depicts the sodium vanillate bound to the column. The lignin contained in the vanillate did not precipitate upon neutralisation with sulphuric acid. The area of the vanillate region was 734 units.

Figure 5:
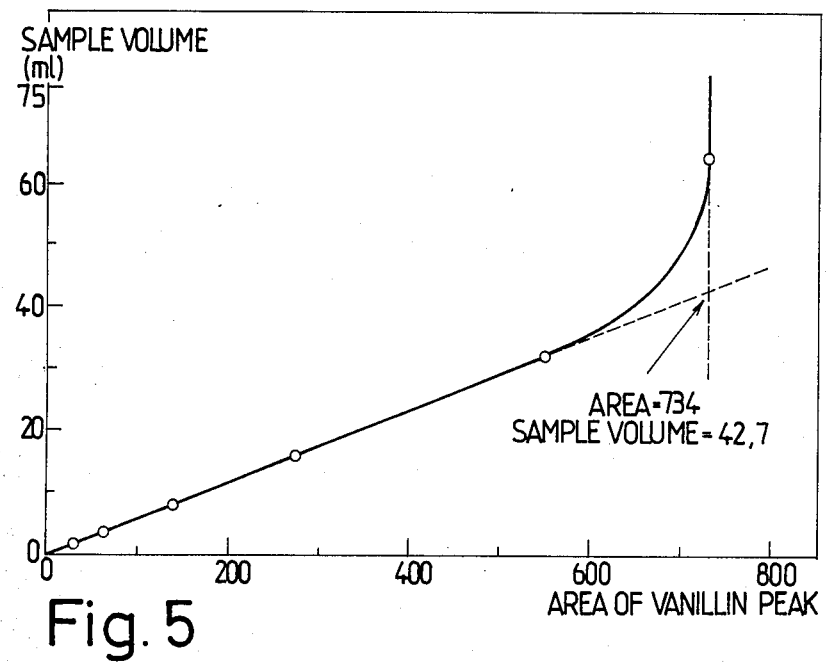

When the planimetered vanillate regions in Examples 1–4 are considered as a function of the sample volume, it can be noted that the area increases linearly as long as there occurs adsorption onto the resin. When the resin no longer is capable of binding more sodium vanillate, the area no more grows despite increases in sample volume. On the basis of Examples 1–4, a curve can be drawn illustrating the relationship between the area of the vanillate region and the sample volume (FIG. 5). From this curve, it can be deduced that the absorption capacity of the ion exchange resin used in the previous examples had been fully utilised at a sample volume of 42,7 ml. Since the sample solution had a content of 9,9 mg vanillin/ml, it can be calculated that the adsorption capacity of the column in respect of sodium vanillate amounted to 423 mg, or 5,4 kg sodium vanillate per cubic meter of resin.

EXAMPLE 5

Figure 6:
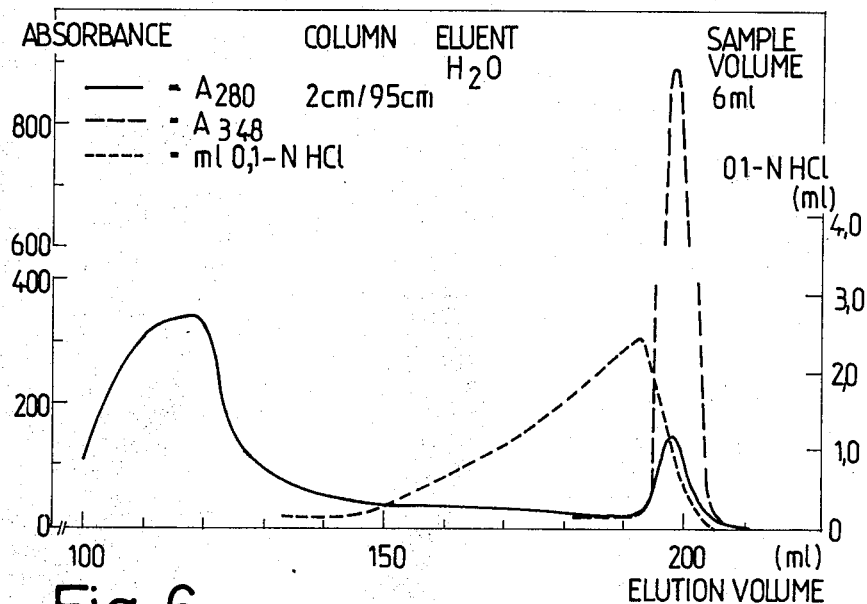

In the 5th example a column was employed whose diameter was 2 cm and length 100 cm. The column was filled with 300 cm$^3$ of Dowex-50W, X-2, 200–400 mesh cation-exchange resin in the sodium form. 6 ml oxidised lignosulphonate solution was fed into the column at the rate of 20 ml/h (6,37 ml/h.cm$^2$), and, after the sample had flowed into the column, distilled water was introduced at the same rate until the column had again become purified. In this experiment it was observed that the lignosulphonate fraction became somewhat extended (elution volume 100–150 ml); however, the vanillate part was distinctly separate from the lignin (the elution volume of the sodium vanillate was 195–205 ml), and the sodium vanillate appeared immediately after the maximum of the alkali concentration (FIG. 6). This test implies that an optimum can be found by changing the volume and diameter of the column, so that the separation of sodium vanillate from lignin is as complete as possible under the experimental conditions applied.

EXAMPLE 6

A column was used with a diameter of 1,09 cm and length 35 cm. The column was filled with 25 cm$^3$ of Dowex-50W, X-8, 200–400 mesh cation-exchange resin in its sodium form. Oxidised lignosulphonate solution with a content of 10,2 mg vanillin/ml was fed into the column at the rate of 25,8 ml/h (27,7 ml/h.cm$^2$), until the adsorption capacity of the resin had been fully consumed. The amount of sodium vanillate bound by the column at the saturation point was calculated. It was established that the cation exchange resin used was capable of adsorbing 5,5 kg sodium vanillate/m$^3$ resin.

EXAMPLE 7

A glass column, diameter 4 cm and length 200 cm, was filled with 2500 cm³ of Dowex-50W, X-8, 200–400 mesh strong sulphonic acid-type cation-exchange resin in the Na⁺-form.

800 ml of oxidised lignosulphonate solution with a content of 22 g vanillin per liter was fed into the column at the rate of 60 ml/h (4,8 ml/h.cm²). After the sample had been introduced, the run was continued by pumping distilled water into the column at the same rate until the column had become purified. The solution that passed the column was collected as 40 ml fractions, which were subjected to spectrophotometric determination of the absorbancies at 280 and 348 nm wavelengths and analysed for their contents of oxidation products and consumption of sulphuric acid on neutralisation.

Figure 7:
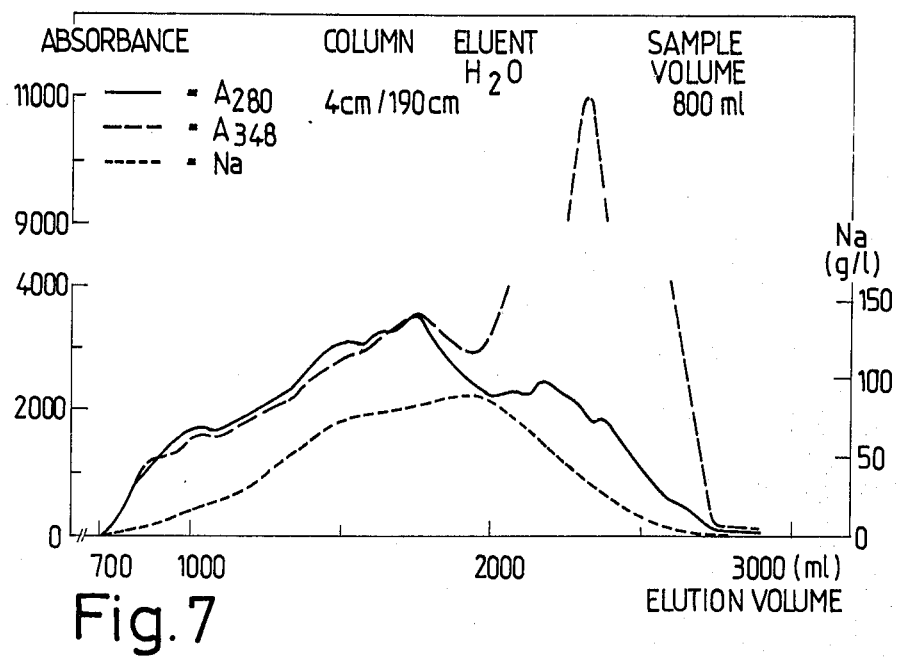

In this test it was noted that the lingosulphonate part was very broad, and that the vanillate part appeared after the lignin area, although these were partly superimposed (FIG. 7). The pH of the lignin area was 12 or higher, while that of the vanillin area ranged from 7 to 12. No precipitation took effect upon neutralisation with sulphuric acid.

The amount of sulphuric acid consumed in the neutralisation of the vanillate area had diminished by 62,5% as compared with the amount of sulphuric acid consumed in the neutralisation of the entire sample. At the peak of the vanillate region, the concentrations of the oxidation products were more than twice as high as those in the original lignosulphonate solution fed into the column. In the elution of the adsorbed oxidation products from the column, the quantity of distilled water required equalled the quantity of oxidised solution introduced in the experiment.

EXAMPLE 8

The procedure of Example 6 was followed, except that the column was filled with Dowex-50W, X-16, 200–400 mesh cation-exchanger in the Na⁺-form. It was established that the column was capable of adsorbing 1.3 kg sodium vanillate per m³ resin.

EXAMPLE 9

The procedure of Example 6 was followed, except that the column was filled with Amberlite-200 macroporous, strong sulphonic acid type cation-exchanger in the Na³⁰-form. It was established that the column was capable of adsorbing 2.4 kg sodium vanillate per m³ resin.

EXAMPLE 10

The procedure of Example 6 was followed, except that the column was filled with AG-MP-50, 200–400 mesh macroporous, strong sulphonic acid-type cation-exchanger in the Na⁺-form (Bio-Rad). It was established in this test that the resin was capable of adsorbing 2,0 kg sodium vanillate per m³.

EXAMPLE 11

The procedure of Example 6 was followed, except that the column was filled with Amberlite-CG-50, 200 mesh macroporous metacrylic acid type weak cation-exchanger in the Na⁺-form. It was noted that the column was capable of adsorbing 2,0 kg sodium vanillate per m³ resin.

EXAMPLE 12

A glass tube, diameter 2 cm and length 40 cm, was filled with 78,5 cm³ of Dowex-50W, X-2, 200–400 mesh strong cation-exchange resin in the Na⁺-form.

4 ml of oxidised lignosulphonate solution, with a vanillin content of 11 mg/l, was introduced into the column at the rate of 20,2 ml/h (6,44 ml/h.cm²). After the sample, 75 ml of an aqueous sodium carbonate solution (1 mole/l) was fed into the column at the same rate. This was followed by introduction of distilled water until all of the substances adsorbed onto the resin had been eluted from the column. The solution that had passed through the column was collected as 4 ml fractions, which were subjected to spectrophotometric determination of the absorbance at wavelengths 280 and 348 nm.

Figure 8:
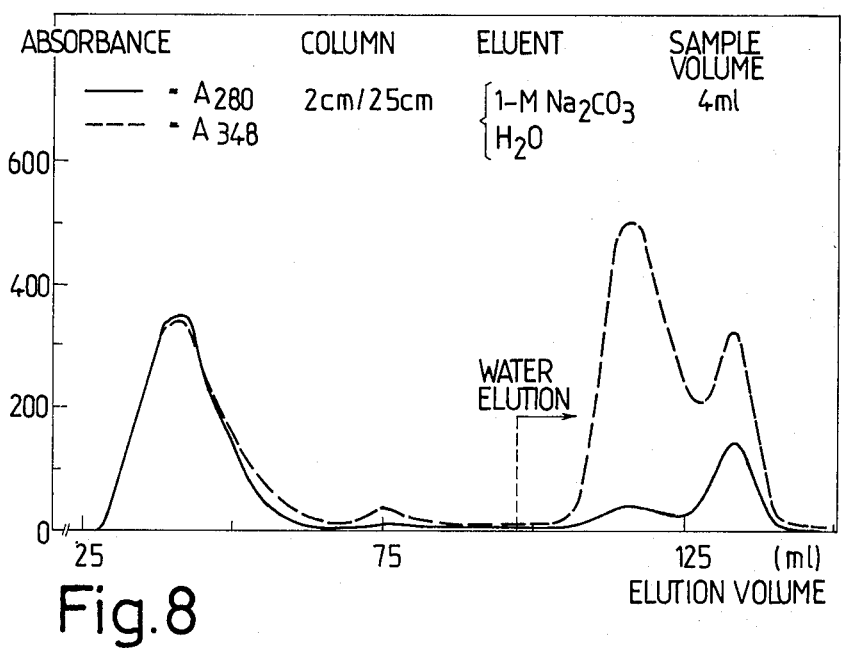

On the basis of this test it was established that the lignin is eluated by the sodium carbonate solution exactly as in the previous examples by water, whereas the oxidation products are eluted more slowly than by water and distinctly after the lignosulphonate part (FIG. 8). Moreover, it was established that as the elution is continued with distilled water, sodium vanillate is the first oxidation product removed from the column, and is followed by the sodium salt of dehydrodivanillin. Upon neutralisation of the vanillate region with sulphuric acid, carbon dioxide was liberated but no precipitation was detectable.

On the basis of the test it was established that the strong cation-exchange resin in the sodium form was capable of removing the oxidation products from the oxidised sodiumlignosulphonate solution, the oxidation products being adsorbed onto the surface of the resin. The object of introduction of sodium carbonate solution into the column, after the sample, was that of purifying the column from the excess of lignin solution. The object of introduction of distilled water was that of eluting the sodium vanillate and related compounds from the column.

On the basis of the above examples it can be stated that the invention is applicable in the separation of oxidation products, by which is understood sodium vanillate, sodium vanillate type aromatic compounds and dimers or trimers formed during the oxidation of lignin, from an oxidised lignin solution that can moreover be collected for further treatment.

By changing the eluant, the oxidation products are furthermore isolable as aromatic monomers, such as sodium vanillate, and other oxidation products formed in the oxidation of lignin, such as the sodium salt of dehydrodivanillin.

We claim:

1. A method for the separation of sodium vanillate from lignin and alkali in alkaline aqueous solutions, comprising the steps of feeding an alkaline aqueous solution containing sodium vanillate and a material selected from the group of lignin and alkali into a bed of a cation exchange resin in its sodium salt form, said sodium vanillate and said material being adsorbed on the resin at different strength levels, and eluting the adsorbed sodium vanillate and said material from the resin by aqueous solution, said sodium vanillate being collected primarily in one elution volume and said material being collected primarily in a second elution volume.

2. The method of claim 1, comprising the step of eluting the sodium vanillate and said material from the resin with an aqueous sodium salt solution, followed by water.

3. The method of claim 1, and including the step of eluting the sodium vanillate and said material from the resin with an aqueous solution of sodium carbonate 4. The method of claim 1, and including the step of utilizing a strong sulphonic acid-type cation exchange resin to adsorb said sodium vanillate and said material.

5. The method of claim 1, and including the step of utilizing a macroporous metacrylic acid-type weak cationic exchange resin to adsorb said sodium vanillate and said material.

6. The method of claim 1, and including the step of maintaining the pH of said aqueous solution at a value above 12.0.

* * * * *